United States Patent [19]

Liburdy

[11] 4,207,075
[45] Jun. 10, 1980

[54] RABBIT IMMUNOGLOBULIN-N-(3-PYRENE)-MALEIMIDE CONJUGATE FOR FLUORESCENT IMMUNOASSAY

[76] Inventor: Robert P. Liburdy, 106 Thornell, San Antonio, Tex. 78235

[21] Appl. No.: 932,094

[22] Filed: Aug. 8, 1978

[51] Int. Cl.$^2$ ............... G01N 33/16; G01N 21/00
[52] U.S. Cl. .................... 23/230 B; 252/408; 260/112 R; 424/8; 424/12
[58] Field of Search ............... 424/8, 12; 23/230 B; 252/408; 260/112 R

[56] References Cited

U.S. PATENT DOCUMENTS

| | | | |
|---|---|---|---|
| 3,720,760 | 3/1973 | Bennich | 424/1 |
| 3,817,706 | 6/1974 | Smith | 23/230 B |
| 3,904,373 | 9/1975 | Harper | 23/253 TP |
| 3,960,840 | 6/1976 | Secrist | 260/211.5 R |
| 4,018,884 | 4/1977 | Cleeland, Jr. | 424/8 |
| 4,036,946 | 7/1977 | Kleinerman | 424/8 |

OTHER PUBLICATIONS

Robert P. Liburdy, J. Immuno. Methods, 28, 243-253 (1979).
R. P. Liburdy et al., Abstract Federation Proceedings, 36:1089 (1977).
R. P. Liburdy et al., Cell Motility, vol. 3, pp. 229-234 (1976).
R. P. Liburdy et al., Abstract, 166th National Meeting Am. Chem. Soc., Chic., Ill., Biol #097, 1973.
J. K. Weltman et al., J. Biol. Chem., 248(9), 3173-3177 (1973).
J. J. Munoz, Anal. Chem., 31 (6), 981-985 (1959).
Chemical Abstracts, 85:59091p (1976).
R. P. Liburdy, Ph. D. Thesis, Brown Univ., Providence, Rhode Island, 1975.

Primary Examiner—Sidney Marantz
Attorney, Agent, or Firm—Joseph E. Rusz; William J. O'Brien

[57] ABSTRACT

A fluorometric technique which uses a detecting fluorophore for determining the quantitative levels of human immunoglobulin. The detecting fluorophore is an N-(3-pyrene)-maleimide conjugated immunoglobulin which shows enhanced quantum yield in the presence of human immunoglobulin molecules. Measuring the resulting changes in fluorescent emission determines the concentration level of the human immunoglobulin present in a test sample since the induced changes in fluorescence are directly proportional to the protein concentration.

5 Claims, 6 Drawing Figures

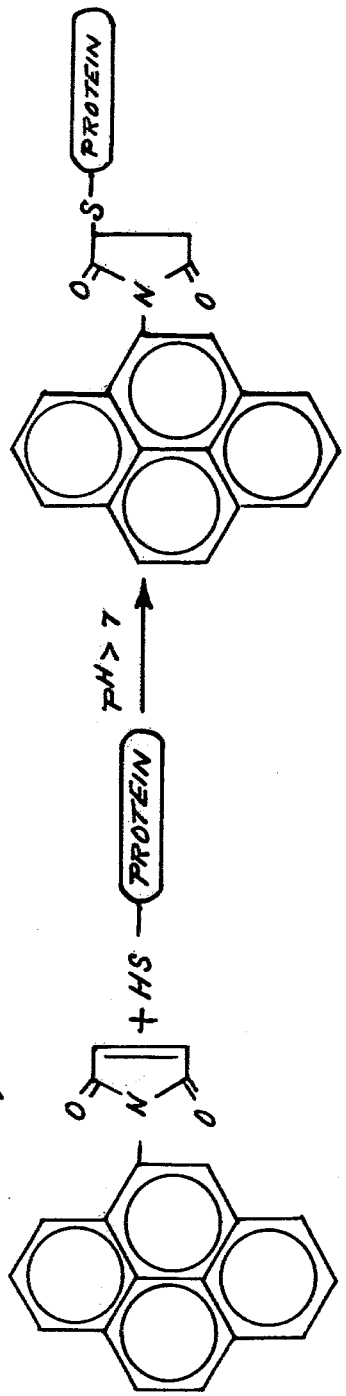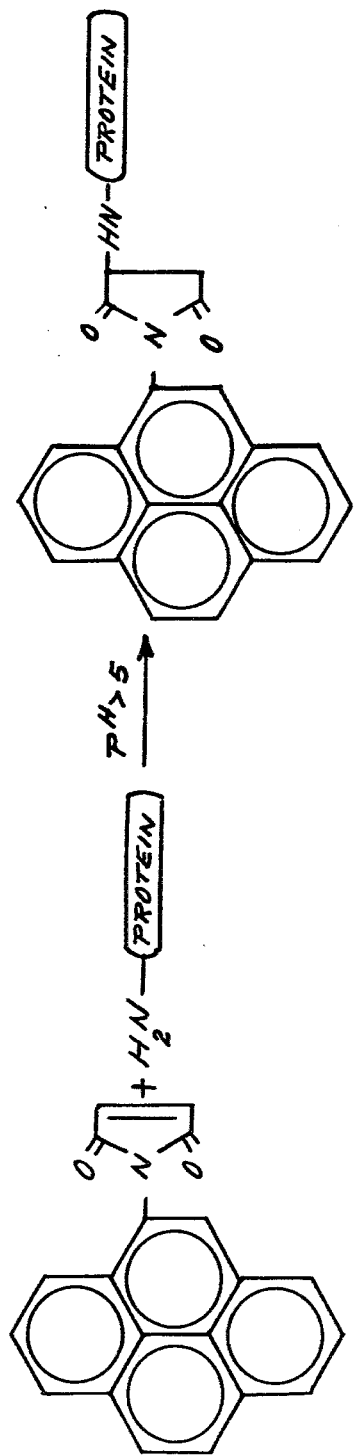
FIG. 1

RABBIT IMMUNOGLOBULIN-N-(3-PYRENE)-MALEIMIDE CONJUGATE FOR FLUORESCENT IMMUNOASSAY

STATEMENT OF GOVERNMENT INTEREST

The invention described herein may be manufactured and used by or for the Government for governmental purposes without the payment of any royalty thereon.

BACKGROUND OF THE INVENTION

This invention relates to a method for determining the quantitative levels of serum or tissue protein. More particularly, this invention concerns itself with the quantitative determination of protein levels by measuring the changes in fluorescence emission of an immunospecific affinity fluorescent agent which is specifically induced by the molecular interactions between a target protein and the fluorescent agent.

At the present time, a significant need exists for a versatile, accurate, rapid, and economical test to quantitate levels of serum and tissue proteins, particularly human immunoglobulin. Radial immunodiffusion, solid-phase immunosorbent, and radioimmuno assays are conventional techniques presently utilized. Although each of these have proven somewhat successful, they all suffer certain disadvantages. In attempting to improve on these prior art methods, various alternative techniques are continually being developed and refined. For example, immunoenzymatic amplification and laser doppler electrokinetics are recent methods conceived for improving protein determinations.

As is well known, fluorescent probes constitute a very useful tool in the study of protein structures because changes in the conformation of the protein conjugate may significantly alter the emission properties of the probe. As a consequence, a research effort has evolved which is directed towards the goal of developing a method for determining protein level concentrations through the use of fluorescent type indicators. The resulting research effort produced the novel immunospecifically-directed fluorescent enhancement technique of this invention which utilizes N-(3-pyrene) maleimide, hereinafter referred to as PM, as the immunospecific fluorescent reagent or fluorescent probe. This novel method provides a simple, rapid and inexpensive, quantitative technique for determining concentration levels of serum or tissue protein, particularly human immunoglobulin, hereinafter referred to as IgG.

SUMMARY OF THE INVENTION

The present invention concerns itself with a method for determining the concentration levels of serum or tissue protein, especially human immunoglobulin, which involves the use of a novel fluorescent immunospecific reagent or fluorophore. The detecting fluorophore is an N-(3-pyrene)-maleimide-conjugated immunoglobulin, hereinafter referred to as PM-RaHIgG. It shows enhanced quantum yield in the presence of target molecules, hence eliminating the need for removing fluorescent-unbound PM-RaHIgG and, thus, making the assay virtually instantaneous. Determination of protein concentration levels is accomplished by titrating the reagent with human immunoglobulin which results in fluorescence enhancement proportional to human immunoglobulin concentration. The concentration, therefore, can then be determined by measuring the fluorescence emission spectrum of a test sample.

The use of the new fluorescent reagent enables quantitation of human IgG by fluorescent enhancement. As was stated heretofore, the working assay is virtually instantaneous since exogenous unbound fluorophore need not be removed from the reaction mixture. In principle, the technique can be made specific for any immunogenic macromolecule. Simplicity and rapidity of the procedure plus its potential versatility make the assay a desirable adjunct to existing methodologies.

Accordingly, the primary object of this invention is to provide a simple, rapid, inexpensive, quantitative, micro-technique for determining the concentration levels of serum or tissue protein.

Another object of this invention is to develop a fluorescent immunospecific affinity reagent for use in determining concentration levels of human immunoglobulin.

Still another object of the invention is to provide a detecting fluorophore that is covalent, affinity-labelled, bifunctional, that can bind a particular target protein, and is capable of exhibiting changes in fluorescence emission that have been specifically induced by the molecular interaction between the detecting reagent and a target protein.

The above and still other objects and advantages of the present invention will become more readily apparent upon consideration of the following detailed disclosure thereof when taken in conjunction with the accompanying drawings.

DESCRIPTION OF THE DRAWINGS

In the drawings:

FIG. 1 is a schematic illustration showing the formation of N-(3-pyrene)maleimide adducts through thiol (ph 5) or amino (ph>7) group conjugation;

DETAILED DESCRIPTION OF THE PREFERRED EMBODIMENT

Figure 2:
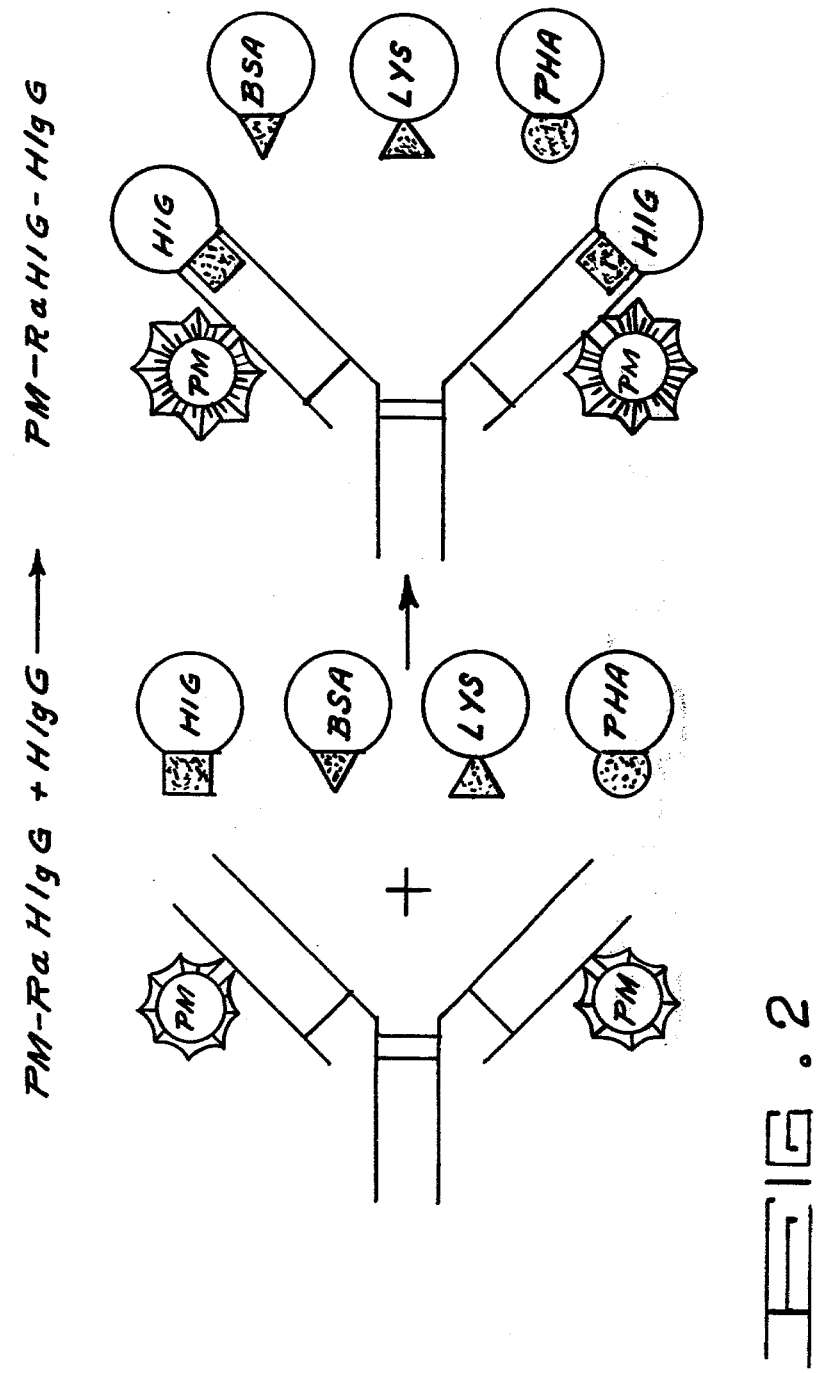
FIG. 2 is a schematic illustration of HIgG binding to PM-RaHIgG.

Pursuant to the above-defined objects, this invention provides a novel immunospecific affinity reagent or detecting fluorophore for use in determining the concentration levels of human immunoglobulin. The method for determining the concentration levels employs an immunospecific protein-protein interaction that induces a change in the fluorescence emission of a fluorescent dye bound to a protein adduct.

To this end, a prototype fluorophore, N-(3-pyrene)-maleimide (PM), is used to generate a fluorescent reagent sensitive to specific protein binding. PM is advantageous because it attaches unilaterally and covalently to free sulfhydryl residues present in proteins, and its conjugates exhibit fluorescence that may be sensitive to protein conformation and, thus, protein binding.

The PM fluorophore is reacted with immunoglobulin to generate the fluorescent PM conjugate immunospecific for detection of a target protein such as human immunoglobulin (HIgG). As a first effort, a PM adduct of immunoglobulin raised against human antibody in rabbit was generated (PM-RaHIgG). The PM-RaHIgG is a covalently labelled, bi-functional, fluorescent, affinity reagent that has a fixed fluorescent indicator (PM) sensitive to perturbation of its micro-environment, and an immunospecific protein moeity (RaHIgG) directed at specifically binding human immunoglobulin.

The determination of the concentration level is performed by introducing a test sample of HIg into a buffered solution of PM-RaHIgG ($10^{-5}$ M in 50 mM PBS, ph 7.5 at 16° C.) and measuring the fluorescence emission spectrum, using incident radiation of 345 nm (the maximum excitation band of PM-RaHIgG), over the emission wavelength range of 300 to 450 nm.

N-(3-pyrene)maleimide is a nonfluorescent pyrene-substituted maleimide that possesses affinity for freely-reactive sulfhydryl and amino group residues in proteins. Upon conjugation, however, PM adducts of muscle proteins, 30S ribosomes, immunoglobulins, and simple thiol model compounds exhibit intense fluorescence.

As illustrated in FIG. 1 of the drawing, N-ethylmaleylation proceeds at PH>5 with free sulfhydryl residues, and at PH>7 with reactive amino groups. The reaction with both of the groups involves an addition of the electrophile across the olefinic double bond of PM. At neutral pH, the sulfhydryl group proceeds at a much faster rate than the amino group. Since immunoglobulins, as a rule, do not possess freely-reduced sulfhydryls, PM-addition reactions with Ig are expected to involve amino group modification.

The enhancement of PM-RaHIgG fluorescence is due to immunospecific binding of HIgG as illustrated in FIG. 2. In this scheme, the site of PM ligand attachment is arbitrarily shown on the Fab fragment of the RaHIgG molecule. Depicted figuratively are PM-RaHIgG and binding sites on HIg, bovine serum albumin (BSA), lysozyme (LYS), and phytohemagglutinin-M)PHA). When PM-RaHIgG and the four proteins are mixed only HIg is specifically bound, leading to an alteration in PM-RaHIgG fluorescence.

Figure 3:
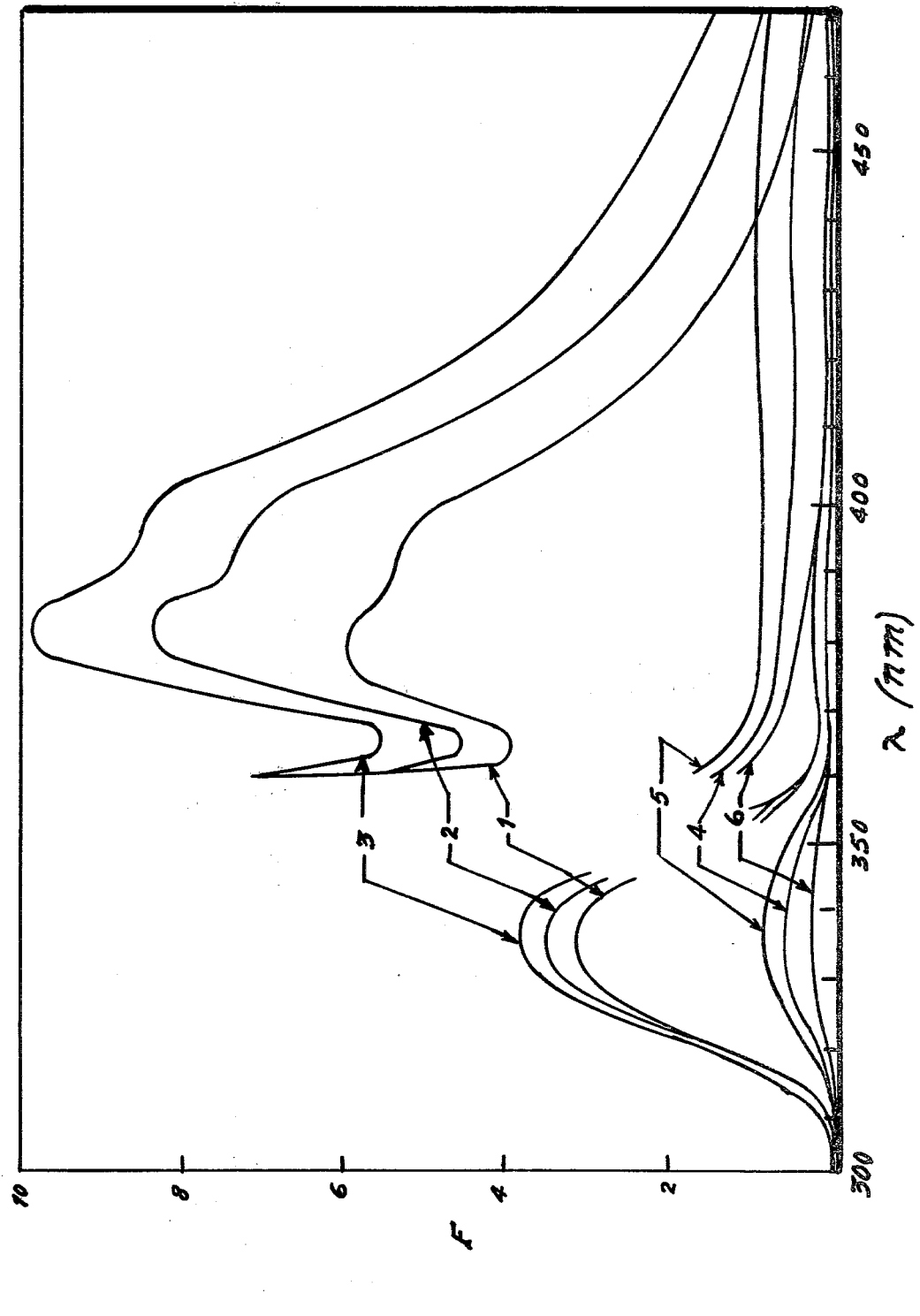
FIG. 3 is a graphical illustration showing the fluorescence emission spectra of PM-RaHIgG in the presence of increasing concentrations of HIgG.

A plot of fluorescence emission intensity against HIgG concentration is shown in FIG. 3. The light-scattering spectra (left-hand side) and fluorescence-emission spectra (right-hand side) of PM-RaHIgG in the presence of increasing concentration of HIgG are shown in FIG. 3. The PM-RaHIgG was at 50.0 mg/ml in 0.1 N NaCl, 50 mM TES, pH 7.2, 25° C. HIgG was added to give 0 mg/ml (Spectrum 1), 2.0 mg/ml (Spectrum 2), and 4.0 mg/ml (Spectrum 3). Emission spectra are also shown for 2.0 mg/ml HIgG (Spectrum 4), 4.0 mg/ml HIgG (Spectrum 5) or buffer alone (Spectrum 6). $\lambda_{ex}$ was 35 nm throughout. Spectrum 1 represents PM-RaHIgG alone. Addition of HIgG to give 2.0 mg/ml and of 4.0 mg/ml results in fluorescent enhancement (Spectra 2 and 3, respectively). Exogenous light scattering and fluorescence due to HIgG alone is minimal and is illustrated in Spectrum 4 (2.0 mg/ml HIgG) and Spectrum 5 (4.0 mg/ml HIgG). Buffer alone shows very little light scattering (Spectrum 6).

Figure 4:
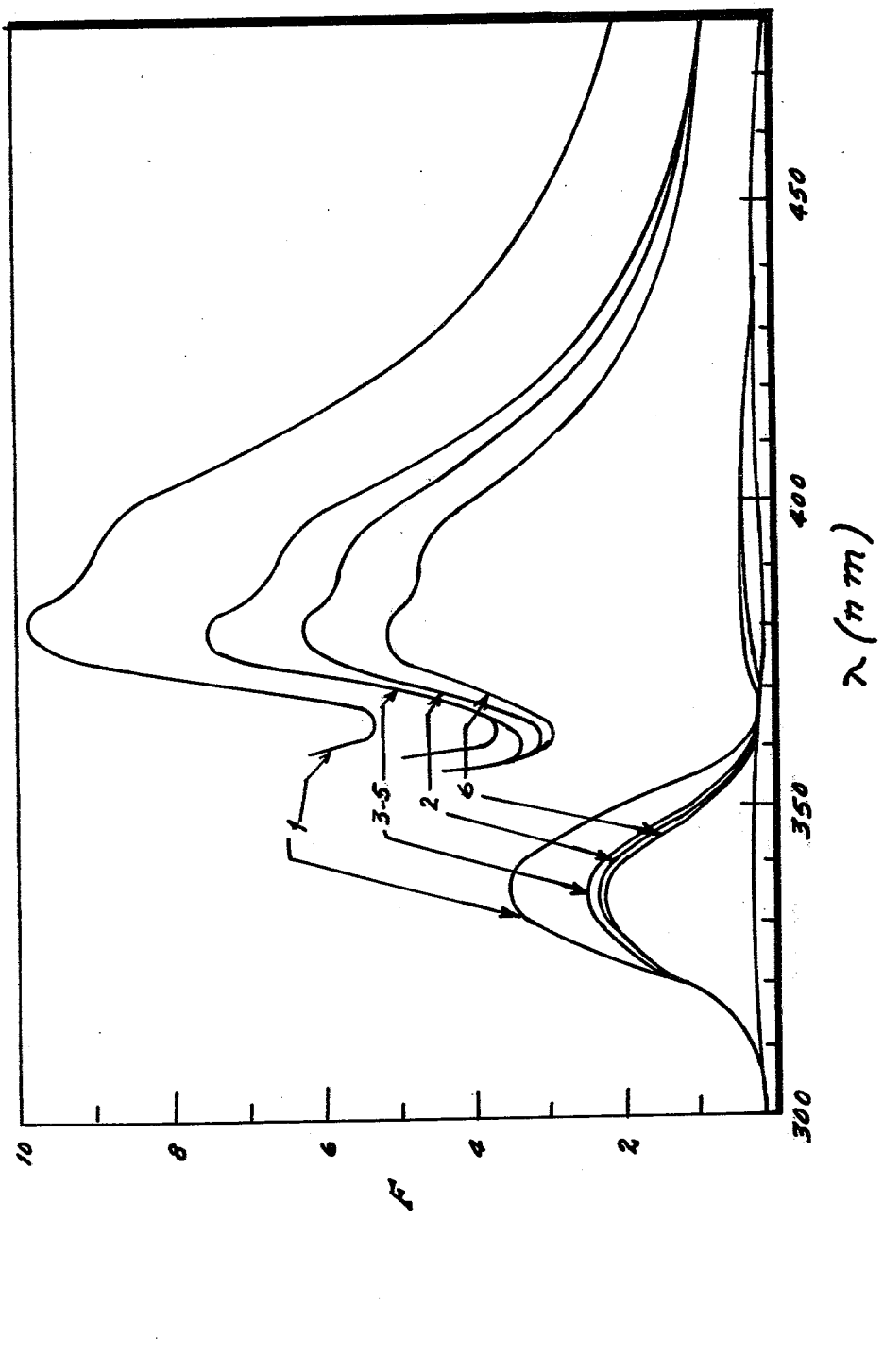
FIG. 4 is a graphical illustration showing the fluorescence emission spectra of PM-RaHIgG in the presence of HIgG, bovine serum albumin (BSA), lysozyme (LYS), or phytohemagglutinin-M (PHA)

To demonstrate that only antigen-antibody interactions may lead to enhancement of PM-RaHIgG fluorescence, the reagent was titrated with bovine serum albumin (BSA), lysozyme (LYS), and phytohemagglutinin-M (PHA), in addition to HIgG. In FIG. 4 is shown the fluorescence-emission spectra of PM-RaHIgG plus HIg (Spectrum 1), PM-RaHIgG plus various concentrations of BSA (2-5), and PM-RaHIgG plus LYS or PHA, or PM-RaHIgG alone (6). Enhancement of PM-RaHIgG fluorescence was observed upon addition of both HIgG or BSA. However, titration experiments showed that addition of BSA to PM-RaHIgG in the presence of HIgG did not result in further enhancement of fluorescence. In contrast, addition of HIgG to PM-RaHIgG plus BSA did result in enhancement to levels obtained with PM-RaHIgG and HIgG alone. Furthermore, immunodiffusion of the reagent PM-RaHIgG against HIgG and BSA gave two precepitin bands of nonidentity, with the HIgG band very strong compared to the faint BSA band. Thus, the fluorescence enhancement induced by BSA may be attributed to weak immunoreactivity of PM-RaHIgG towards BSA. Since HIgG prevents BSA enhancement of PM-RaHIgG but not the reverse, HigG and BSA probably compete for distinct antigenic sites that cannot be occupied simultaneously by their respective antigens. The HIgG molecules most likely possess a greater binding constant for PM-RaHIgG than do BSA molecules, since HIgG is able to associate with PM-RaHIgG and lead to enhancement in the presence of BSA.

Conditions for the data set forth in FIG. 4 are the same as in FIG. 3. The PM-RaHIgG (Spectrum 6) was titrated with HIgG to give 2.0 mg/ml (Spectrum 1); or with BSA to give 2.0 (Spectrum 2), 4.0, 4.0, 5.0 (Spectrum 3 to 5) mg/ml; or with PHA or LYS to give 2.0 mg/ml (Spectrum 5).

Figure 5:
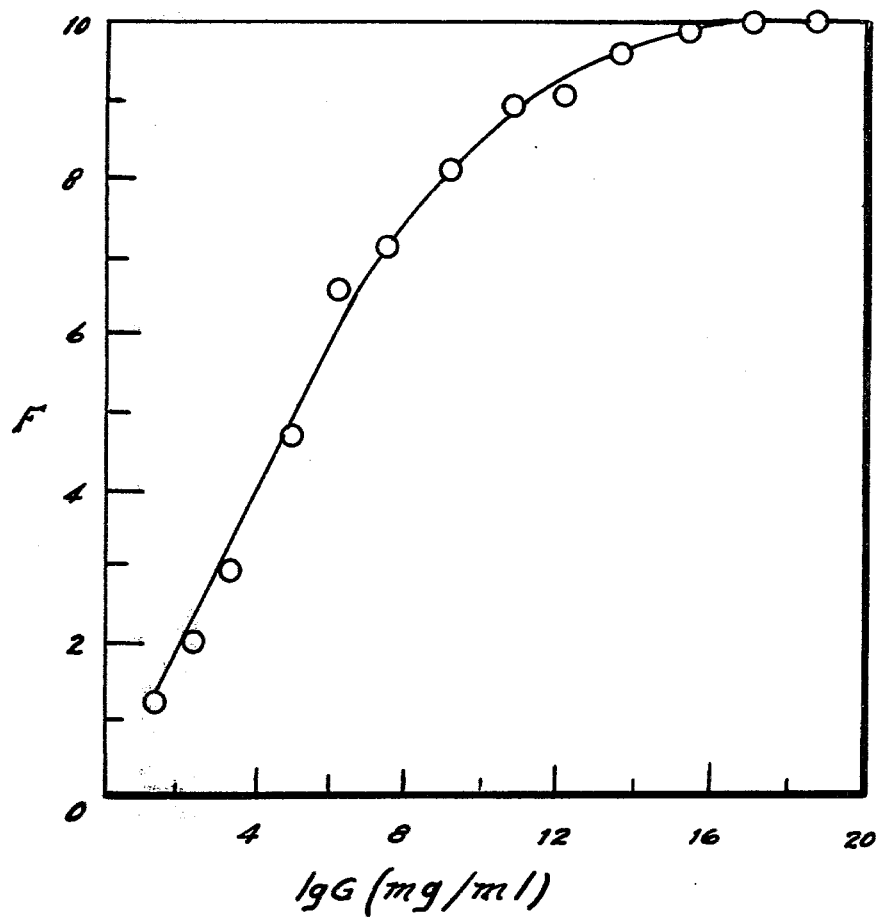
FIG. 5 is a graphical illustration showing the fluorescence intensity (F) of PM-RaHIgG at 380 nm plotted against added concentration of HIgG.
Figure 6:
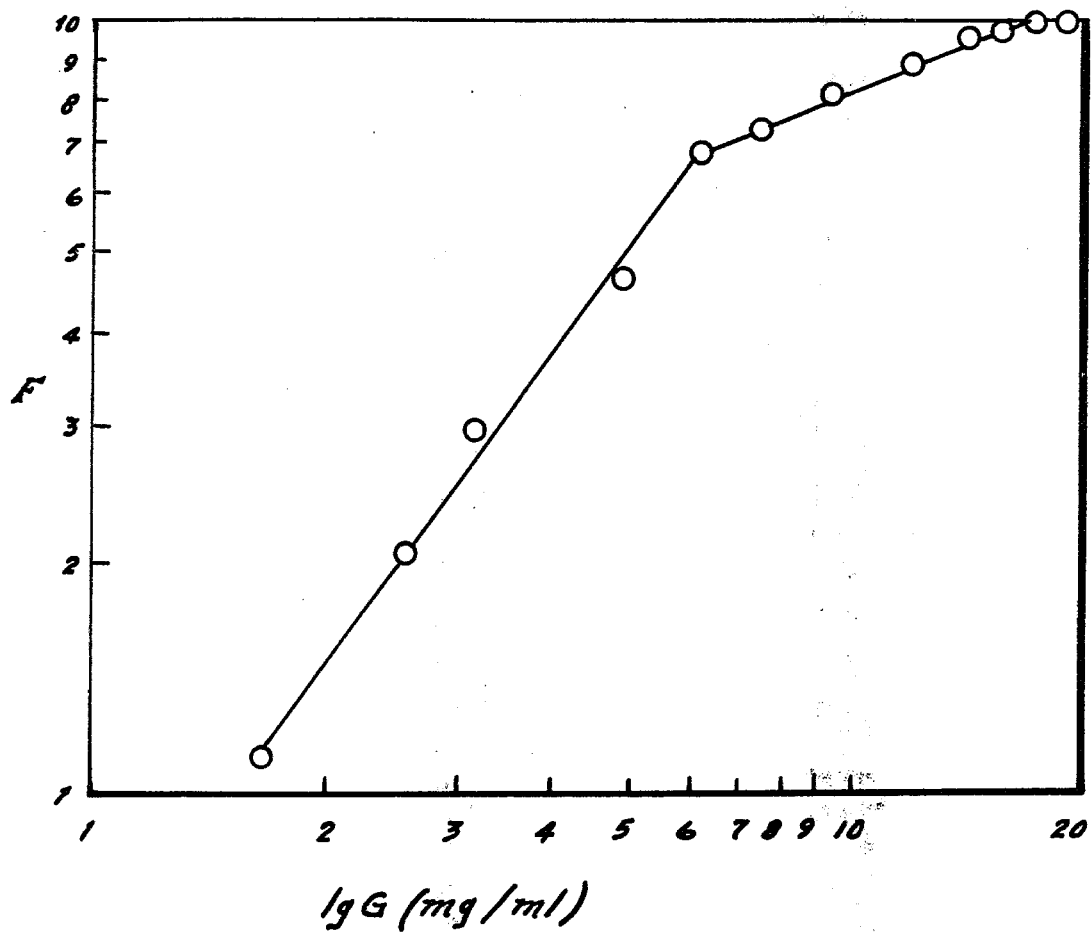
FIG. 6 is a graphical illustration showing a log-log plot of fluorescence intensity of PM-RaHIgG versus HIgG concentration.

Fluorescence emission intensity at 380 nm plotted against the concentration of added HIgG, as illustrated in FIG. 5, shows that there is a linear increase in fluorescence for 2.0–8.0 mg/ml HIgG. At higher concentration of HIgG, fluorescence increases, in a nonlinear monotonic fashion, and appears to saturate at HIgG concentrations in excess of 16.0 mg. The assay conditions were the same as those in FIG. 3. In FIG. 6 is shown a log-log plot of fluorescence versus HIgG concentration. The data was taken from FIG. 5. A straight line is revealed with a break point at 6.0 mg/ml HIgG. The change in slope at relatively high concentration of HIgG may reflect two or more distinct binding sites for HIgG on PM-RaHIgG that are titrated separately as HIgG concentration is increased. Nevertheless, the linear relationship between log (F) and log (HIgG concentration) observed at relatively low levels of HIgG (<6.0 mg/ml) indicates that the technique may be useful for the quantitative assay of HIgG at the milligram level.

Results from a limited preliminary comparison of the PM-fluorometric assay of this invention, designated Fluor-Stat (FS), with a solid-phase bead assay (IF, Bio-rad) and a radial immunodiffusion assay (RID, Cappel) are shown in Table I. For the six serum samples tested, HIgG values from the Fluoro-Stat assay were within 8 percent or better of the other reported results. This limited comparative study suggests that the Fluoro-Stat assay may prove useful in detecting HIgG at the milligram level.

TABLE I

MEASUREMENT OF HIgG BY FLUORO-STAT (FS), RADIAL IMMUNO DIFFUSION (RID), AND SOLID-PHASE BEAD (IF) ASSAYS

| Human Serum | Measured HigG (Mean ± SD; N = 3 (mg/ml) | | |
|---|---|---|---|
| | FS[a] | RID[b] (Δ%)[d] | IF[c] (Δ%)[d] |
| 1 | 53.7 ± 1.1 | 51.2 ± 2.3 (4.8%) | 56.9 ± 4.6 (5.6%) |
| 2 | 194.6 ± 3.1 | 186.7 ± 5.1 (4.2%) | 191.9 ± 5.2 (1.4%) |
| 3 | 119.3 ± 4.2 | 121.0 ± 4.1 (1.4%) | 115.8 ± 6.0 (3.0%) |
| 4 | 49.6 ± 1.9 | 51.4 ± 2.1 (3.5%) | 53.8 ± 3.7 (7.8%) |
| 5 | 96.1 ± 4.1 | 89.9 ± 3.2 (6.8%) | 94.2 ± 4.3 (2.0%) |
| 6 | 110.1 ± 5.1 | 119.4 ± 7.1 (7.7%) | 118.2 ± 6.2 (6.8%) |

[a]FS: Fluoro-Stat assay
[b]RID: Radial immunodiffusion
[c]IF Solid-phase bead assay
[d]Δ% Percent change with respect to FS The N-(3-pyrene)maleimide component used in this invention was prepared according to conventional techniques. The human gamma immunoglobulin, HIgG, was isolated from human serum by ammonium sulfate precipitation followed by purification on a G-200 Sephadex column. The immunoglobulin fraction of immunospecific rabbit antihuman IgG antiserum (RaHIgG) was conjugated to PM as follows: RaHIgG (1 mg/ml) was incubated at 4° C. on ice for 30 minutes with gentle stirring and then titrated with PM ($3 \times 10^{-3}$ M in acetone) to a final concentration of $3 \times 10^{-5}$ M. After an additional 30 minutes, free PM was quenched by the addition of B-mercaptoethanol to $10^{-2}$ M. The conjugated antisera was then desalted by a single pass over a bed of G-25 Sephadex.

The bovine serum albumin (BSA), phytohemagglutinin-M (PHA), and lysozyme (LYS) were purchased from commercial sources. Glass-distilled deionized water was used throughout.

The fluorescence spectra data was recorded on an Aminco-Bowman spectrophotofluorometer operating in the ratio mode. Sample cuvettes were placed in a water-jacketed copper block maintained at 25°±0.02° C. during measurements.

The fluorescence assay employing the PM-RaHIgG conjugate was performed by simply titrating the reagent PM-RaHIgG with test serum or stock standards of HIgG and measuring fluorescence intensity. A test sample of HIg was introduced into a buffered solution of PM-RaHIgG ($10^{-5}$ M in 50 nm PBS pH 7.5 at 16° C.) and measuring the fluorescence emission spectrum using incident radiation of 345 nm (the maximum excitation band of PM-RaHIgG), over the emission wavelength range of 300 to 450 nm. In addition, human serum IgG was detected by the Immuno-Fluor assay procedure of the Bio-Rad Laboratories of Richmond, CA or by the radial immunodiffusion technique of the Cappel Laboratories of Cochranville, PA.

Although the present invention is primarily directed toward determining concentration levels of human immunoglobulin, it should be understood that the method of this invention can be made specific for any macromolecule against which antisera can be used.

It should be understood also, that while the present invention has been described by reference to a specific embodiment thereof, various alterations and modifications of the invention may be resorted to and that all such modifications fall within the scope of the appended claims are intended to be included herein.

What is claimed is:

1. A fluorescent immunospecific affinity reagent indicator useful in determining the concentration of human immunoglobulin in a sample which comprises a conjugate of an immunospecific rabbit antihuman immunoglobulin with N-(3-pyrene)maleimide.

2. A method for producing the reagent indicator of claim 1 comprising:
   a. incubating the immunoglobulin fraction of an immunospecific rabbit antihuman antiserum;
   b. titrating said fraction with N-(3-pyrene)maleimide;
   c. quenching free N-(3-pyrene)maleimide by the addition of B-mercaptoethanol; and
   d. desalting and separating the conjugated antiserum.

3. A method for determining the concentration of human immunoglobulin in a human serum sample which comprises the steps of:
   a. mixing said sample of human serum with the reagent indicator of claim 1;
   b. measuring the fluorescence spectrum emitting from the mixture resulting from step a by using incident radiation; and
   c. quantitatively analyzing the resulting fluorescent measurements to indicate the concentration of human immunoglobulin present in said human serum sample.

4. A method in accordance with claim 3 wherein said fluorescent spectrum is measured by using incident radiation with an excitation wavelength of 345 nm over an emission wavelength range of 300 to 400 nm.

5. A method in accordance with claim 3 wherein said mixture is maintained at a temperature of about 16° centigrade and a pH of about 7.5.

* * * * *